US010039938B2

(12) United States Patent
Barthe et al.

(10) Patent No.: US 10,039,938 B2
(45) Date of Patent: *Aug. 7, 2018

(54) SYSTEM AND METHOD FOR VARIABLE DEPTH ULTRASOUND TREATMENT

(71) Applicant: Guided Therapy Systems, LLC, Mesa, AZ (US)

(72) Inventors: Peter G. Barthe, Phoenix, AZ (US); Michael H. Slayton, Tempe, AZ (US)

(73) Assignee: GUIDED THERAPY SYSTEMS, LLC, Mesa, AZ (US)

(*) Notice: Subject to any disclaimer, the term of this patent is extended or adjusted under 35 U.S.C. 154(b) by 1044 days.

This patent is subject to a terminal disclaimer.

(21) Appl. No.: 14/264,732

(22) Filed: Apr. 29, 2014

(65) Prior Publication Data

US 2014/0236049 A1 Aug. 21, 2014

Related U.S. Application Data

(63) Continuation of application No. 12/834,754, filed on Jul. 12, 2010, now Pat. No. 8,708,935, which is a (Continued)

(51) Int. Cl.
*A61B 8/00* (2006.01)
*A61N 7/00* (2006.01)
(Continued)

(52) U.S. Cl.
CPC ............ *A61N 7/00* (2013.01); *A61B 34/30* (2016.02); *A61B 2017/22024* (2013.01);
(Continued)

(58) Field of Classification Search
CPC  A61B 2017/22024; A61B 2017/22028; A61B 34/30; A61N 2007/0065; A61N 2007/0069

See application file for complete search history.

(56) References Cited

U.S. PATENT DOCUMENTS 2,427,348 A   9/1947  Bond et al.
3,913,386 A  10/1975  Saglio
(Continued)

FOREIGN PATENT DOCUMENTS

DE   4029175    3/1992
DE  10140064    3/2003
(Continued)

OTHER PUBLICATIONS

PCT International Search Report and Written Opinion, PCT/US2014/030779, dated Sep. 1, 2014, 8 pages.
(Continued)

*Primary Examiner* — Baisakhi Roy
(74) *Attorney, Agent, or Firm* — Quarles & Brady LLP

(57) ABSTRACT

A non-invasive variable depth ultrasound treatment method and system comprises a variable depth transducer system configured for providing ultrasound treatment to a patient. An exemplary variable depth transducer system can comprise a transducer configured to provide treatment to more than one region of interest, such as between a deep treatment region of interest and a superficial region of interest, and/or a subcutaneous region of interest. The variable depth transducer can comprise a transduction element having a piezoelectrically active layer, matching layers and/or other materials for generating radiation or acoustical energy. The variable depth transducer may be configured to operate at moderate frequencies within the range from approximately 750 kHz to 20 MHz or more. In addition, the transduction element may be configured with a variable depth device comprising one or more materials configured to allow for control and focusing/defocusing of the acoustic energy to more than one region of interest.

20 Claims, 9 Drawing Sheets

Related U.S. Application Data continuation of application No. 10/944,500, filed on Sep. 16, 2004, now Pat. No. 7,824,348.

(51) Int. Cl.
   A61B 17/22 (2006.01)
   A61B 34/30 (2016.01)

(52) U.S. Cl.
   CPC .......... A61B 2017/22028 (2013.01); A61N 2007/0065 (2013.01); A61N 2007/0069 (2013.01); A61N 2007/0073 (2013.01); A61N 2007/0095 (2013.01)

(56) References Cited

U.S. PATENT DOCUMENTS

| | | |
|---|---|---|
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,166,967 A | 9/1979 | Benes et al. |
| 4,211,948 A | 7/1980 | Brisken et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A * | 4/1982 | Glenn ............ A61B 8/00 600/446 |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Tanezer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller et al. |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggers et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough et al. |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry et al. |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh et al. |
| 4,917,096 A | 4/1990 | Englehart |
| 4,973,096 A | 4/1990 | Jaworski |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry et al. |
| 5,040,537 A | 8/1991 | Katakura |
| 5,054,310 A * | 10/1991 | Flynn ............ G01D 18/00 73/1.86 |
| 5,054,470 A | 10/1991 | Fry et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi et al. |
| 5,123,418 A | 6/1992 | Saurel |
| 5,143,063 A | 9/1992 | Feltner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada et al. |
| 5,269,297 A | 12/1993 | Weng |
| 5,282,797 A | 2/1994 | Chess |
| 5,295,484 A | 3/1994 | Marcus et al. |
| 5,295,486 A | 3/1994 | Wollschlaeger et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi |
| 5,370,121 A | 12/1994 | Reichenberger et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |

(56) References Cited

U.S. PATENT DOCUMENTS

| | | |
|---|---|---|
| 5,419,327 A | 5/1995 | Rohwedder |
| 5,423,220 A | 6/1995 | Finsterwald et al. |
| 5,435,311 A | 7/1995 | Umemura et al. |
| 5,438,998 A | 8/1995 | Hanafy |
| 5,458,596 A | 10/1995 | Lax |
| 5,460,179 A | 10/1995 | Okunuki et al. |
| 5,460,595 A | 10/1995 | Hall et al. |
| 5,469,854 A | 11/1995 | Unger et al. |
| 5,471,488 A | 12/1995 | Fujio |
| 5,487,388 A | 1/1996 | Rello et al. |
| 5,492,126 A | 2/1996 | Hennige et al. |
| 5,496,256 A | 3/1996 | Bock |
| 5,501,655 A | 3/1996 | Rolt et al. |
| 5,503,152 A | 4/1996 | Oakley et al. |
| 5,503,320 A | 4/1996 | Webster et al. |
| 5,507,790 A | 4/1996 | Weiss |
| 5,520,188 A * | 5/1996 | Hennige ............... A61B 8/0833 310/367 |
| 5,522,869 A | 6/1996 | Burdette et al. |
| 5,523,058 A * | 6/1996 | Umemura ................ A61N 7/02 134/1 |
| 5,524,620 A | 6/1996 | Rosenschein |
| 5,524,624 A | 6/1996 | Tepper |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz et al. |
| 5,529,070 A | 6/1996 | Augustine et al. |
| 5,540,235 A | 7/1996 | Wilson |
| 5,558,092 A | 9/1996 | Unger et al. |
| 5,560,362 A | 10/1996 | Sliwa et al. |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon et al. |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine |
| 5,657,760 A | 8/1997 | Ying et al. |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi et al. |
| 5,685,820 A | 11/1997 | Riek et al. |
| 5,687,737 A | 11/1997 | Branham et al. |
| 5,690,608 A | 11/1997 | Watanabe |
| 5,694,936 A | 12/1997 | Fujimoto et al. |
| 5,697,897 A | 12/1997 | Buchholtz et al. |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki et al. |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law et al. |
| 5,763,886 A | 6/1998 | Schulte |
| 5,769,790 A | 6/1998 | Watkins et al. |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle et al. |
| 5,827,204 A | 10/1998 | Grandia et al. |
| 5,839,751 A | 11/1998 | Bonin |
| 5,840,032 A | 11/1998 | Hatfield et al. |
| 5,844,140 A * | 12/1998 | Seale ...................... A61B 8/08 310/90.5 |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,876,431 A | 3/1999 | Spehr et al. |
| 5,879,303 A | 3/1999 | Averkiou et al. |
| 5,882,557 A | 3/1999 | Hayakawa |
| 5,891,034 A | 4/1999 | Bucholz |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schaetzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fulmer |
| 5,971,949 A | 10/1999 | Levin |
| 5,977,538 A | 11/1999 | Unger et al. |
| 5,984,882 A | 11/1999 | Rosenschein et al. |
| 5,990,598 A | 11/1999 | Sudol et al. |
| 5,992,236 A * | 11/1999 | White ................. G01N 29/043 73/622 |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe |
| 6,039,048 A | 3/2000 | Silberg |
| 6,039,689 A | 3/2000 | Lizzi |
| 6,042,556 A * | 3/2000 | Beach ...................... A61N 7/02 600/437 |
| 6,049,159 A | 4/2000 | Barthe |
| 6,050,943 A | 4/2000 | Slayton et al. |
| 6,059,727 A | 5/2000 | Fowlkes |
| 6,071,239 A | 6/2000 | Cribbs et al. |
| 6,080,108 A | 6/2000 | Dunham |
| 6,083,148 A | 7/2000 | Williams |
| 6,086,535 A | 7/2000 | Ishibashi et al. |
| 6,086,580 A | 7/2000 | Mordon et al. |
| 6,090,054 A | 7/2000 | Tagishi |

(56) References Cited

U.S. PATENT DOCUMENTS

| | | | |
|---|---|---|---|
| 6,093,883 A | 7/2000 | Sanghvi | |
| 6,101,407 A | 8/2000 | Groezinger | |
| 6,106,469 A | 8/2000 | Suzuki et al. | |
| 6,113,558 A | 9/2000 | Rosenschein et al. | |
| 6,113,559 A | 9/2000 | Klopotek | |
| 6,120,452 A | 9/2000 | Barthe | |
| 6,123,081 A | 9/2000 | Durette | |
| 6,126,619 A | 10/2000 | Peterson et al. | |
| 6,135,971 A | 10/2000 | Hutchinson et al. | |
| 6,139,499 A | 10/2000 | Wilk | |
| 6,159,150 A | 12/2000 | Yale et al. | |
| 6,171,244 B1 | 1/2001 | Finger et al. | |
| 6,176,840 B1 | 1/2001 | Nishimura | |
| 6,183,426 B1 | 2/2001 | Akisada | |
| 6,183,502 B1 | 2/2001 | Takeuchi | |
| 6,183,773 B1 | 2/2001 | Anderson | |
| 6,190,323 B1 | 2/2001 | Digs | |
| 6,190,336 B1 | 2/2001 | Duarte | |
| 6,193,658 B1 | 2/2001 | Wendelken et al. | |
| 6,210,327 B1 | 4/2001 | Brackett et al. | |
| 6,213,948 B1 | 4/2001 | Barthe | |
| 6,216,029 B1 | 4/2001 | Paltieli | |
| 6,233,476 B1 | 5/2001 | Strommer et al. | |
| 6,234,990 B1 | 5/2001 | Rowe et al. | |
| 6,241,753 B1 | 6/2001 | Knowlton | |
| 6,246,898 B1 | 6/2001 | Vesely et al. | |
| 6,251,074 B1 * | 6/2001 | Averkiou | A61B 8/08 600/447 |
| 6,251,088 B1 | 6/2001 | Kaufman et al. | |
| 6,268,405 B1 | 7/2001 | Yao | |
| 6,273,864 B1 | 8/2001 | Duarte | |
| 6,280,402 B1 | 8/2001 | Ishibashi et al. | |
| 6,287,257 B1 | 9/2001 | Matichuk | |
| 6,296,619 B1 | 10/2001 | Brisken | |
| 6,301,989 B1 | 10/2001 | Brown et al. | |
| 6,309,355 B1 | 10/2001 | Cain et al. | |
| 6,311,090 B1 | 10/2001 | Knowlton | |
| 6,315,741 B1 * | 11/2001 | Martin | A61B 8/4254 601/3 |
| 6,322,509 B1 | 11/2001 | Pan et al. | |
| 6,322,532 B1 | 11/2001 | D'Sa | |
| 6,325,540 B1 | 12/2001 | Lounsberry et al. | |
| 6,325,758 B1 | 12/2001 | Carol et al. | |
| 6,325,769 B1 | 12/2001 | Klopotek | |
| 6,325,798 B1 | 12/2001 | Edwards et al. | |
| 6,338,716 B1 | 1/2002 | Hossack et al. | |
| 6,350,276 B1 | 2/2002 | Knowlton | |
| 6,356,780 B1 | 3/2002 | Licato et al. | |
| 6,361,531 B1 | 3/2002 | Hissong | |
| 6,370,411 B1 | 4/2002 | Osadchy et al. | |
| 6,375,672 B1 | 4/2002 | Aksan | |
| 6,377,854 B1 | 4/2002 | Knowlton | |
| 6,377,855 B1 | 4/2002 | Knowlton | |
| 6,381,497 B1 | 4/2002 | Knowlton | |
| 6,381,498 B1 | 4/2002 | Knowlton | |
| 6,387,380 B1 | 5/2002 | Knowlton | |
| 6,390,982 B1 | 5/2002 | Bova et al. | |
| 6,405,090 B1 | 6/2002 | Knowlton | |
| 6,409,720 B1 | 6/2002 | Hissong | |
| 6,413,216 B1 | 7/2002 | Cain et al. | |
| 6,413,253 B1 | 7/2002 | Koop | |
| 6,413,254 B1 | 7/2002 | Hissong | |
| 6,419,648 B1 | 7/2002 | Vitek | |
| 6,423,007 B2 | 7/2002 | Lizzi et al. | |
| 6,425,865 B1 | 7/2002 | Salcudean | |
| 6,425,867 B1 | 7/2002 | Vaezy et al. | |
| 6,425,912 B1 | 7/2002 | Knowlton | |
| 6,428,477 B1 | 8/2002 | Mason | |
| 6,428,532 B1 | 8/2002 | Doukas | |
| 6,430,446 B1 | 8/2002 | Knowlton | |
| 6,432,057 B1 | 8/2002 | Mazess et al. | |
| 6,432,067 B1 | 8/2002 | Martin et al. | |
| 6,432,101 B1 | 8/2002 | Weber | |
| 6,436,061 B1 | 8/2002 | Costantino | |
| 6,438,424 B1 | 8/2002 | Knowlton | |
| 6,440,071 B1 | 8/2002 | Slayton | |
| 6,440,121 B1 | 8/2002 | Weber | |
| 6,443,914 B1 | 9/2002 | Constantino | |
| 6,453,202 B1 | 9/2002 | Knowlton | |
| 6,461,378 B1 | 10/2002 | Knowlton | |
| 6,470,216 B1 | 10/2002 | Knowlton | |
| 6,488,626 B1 | 12/2002 | Lizzi et al. | |
| 6,491,657 B2 | 12/2002 | Rowe | |
| 6,500,121 B1 | 12/2002 | Slayton | |
| 6,500,141 B1 | 12/2002 | Ilion | |
| 6,508,774 B1 | 1/2003 | Acker et al. | |
| 6,511,427 B1 | 1/2003 | Sliwa, Jr. et al. | |
| 6,511,428 B1 | 1/2003 | Azuma | |
| 6,514,244 B2 | 2/2003 | Pope | |
| 6,517,484 B1 | 2/2003 | Wilk et al. | |
| 6,524,250 B1 | 2/2003 | Weber | |
| 6,666,835 B2 | 3/2003 | Martin | |
| 6,540,679 B2 | 4/2003 | Slayton | |
| 6,540,685 B1 | 4/2003 | Rhoads et al. | |
| 6,540,700 B1 | 4/2003 | Fujimoto et al. | |
| 6,554,771 B1 | 4/2003 | Buil et al. | |
| 6,569,099 B1 | 5/2003 | Babaev | |
| 6,569,108 B2 | 5/2003 | Sarvazyan et al. | |
| 6,572,552 B2 | 6/2003 | Fukukita | |
| 6,575,956 B1 | 6/2003 | Brisken et al. | |
| 6,595,934 B1 | 7/2003 | Hissong | |
| 6,599,256 B1 | 7/2003 | Acker | |
| 6,607,498 B2 | 8/2003 | Eshel | |
| 6,618,620 B1 | 9/2003 | Freundlich et al. | |
| 6,623,430 B1 | 9/2003 | Slayton | |
| 6,626,854 B2 | 9/2003 | Friedman | |
| 6,626,855 B1 | 9/2003 | Weng et al. | |
| 6,638,226 B2 | 10/2003 | He et al. | |
| 6,645,162 B2 | 11/2003 | Friedman | |
| 6,662,054 B2 | 12/2003 | Kreindel | |
| 6,663,627 B2 | 12/2003 | Francischelli | |
| 6,665,806 B1 | 12/2003 | Shimizu | |
| 6,669,638 B1 | 12/2003 | Miller et al. | |
| 6,685,640 B1 | 2/2004 | Fry | |
| 6,692,450 B1 | 2/2004 | Coleman | |
| 6,699,237 B2 | 3/2004 | Weber | |
| 6,716,184 B2 | 4/2004 | Vaezy et al. | |
| 6,719,449 B1 | 4/2004 | Laughlin | |
| 6,719,694 B2 | 4/2004 | Weng et al. | |
| 6,726,627 B1 | 4/2004 | Lizzi et al. | |
| 6,825,176 B2 | 4/2004 | Mourad | |
| 6,733,449 B1 | 5/2004 | Krishnamurthy et al. | |
| 6,749,624 B2 | 6/2004 | Knowlton | |
| 6,773,409 B2 | 8/2004 | Truckai et al. | |
| 6,775,404 B1 | 8/2004 | Pagoulatos et al. | |
| 6,790,187 B2 | 9/2004 | Thompson et al. | |
| 6,824,516 B2 | 11/2004 | Batten et al. | |
| 6,835,940 B2 | 12/2004 | Morikawa et al. | |
| 6,846,290 B2 | 1/2005 | Lizzi et al. | |
| 6,875,176 B2 | 4/2005 | Mourad et al. | |
| 6,882,884 B1 | 4/2005 | Mosk et al. | |
| 6,887,239 B2 | 5/2005 | Elstrom et al. | |
| 6,889,089 B2 | 5/2005 | Behl | |
| 6,896,657 B2 | 5/2005 | Willis | |
| 6,902,536 B2 | 6/2005 | Manna et al. | |
| 6,905,466 B2 | 6/2005 | Salgo | |
| 6,918,907 B2 | 7/2005 | Kelly | |
| 6,920,883 B2 | 7/2005 | Bessette | |
| 6,921,371 B2 | 7/2005 | Wilson | |
| 6,932,771 B2 | 8/2005 | Whitmore | |
| 6,932,814 B2 | 8/2005 | Wood | |
| 6,936,044 B2 | 8/2005 | McDaniel | |
| 6,936,046 B2 | 8/2005 | Hissong | |
| 6,945,937 B2 | 9/2005 | Culp et al. | |
| 6,948,843 B2 | 9/2005 | Laugharn et al. | |
| 6,953,941 B2 | 10/2005 | Nakano et al. | |
| 6,958,043 B2 | 10/2005 | Hissong | |
| 6,971,994 B1 | 12/2005 | Young et al. | |
| 6,974,417 B2 | 12/2005 | Lockwood et al. | |
| 6,976,492 B2 | 12/2005 | Ingle | |
| 6,992,305 B2 | 1/2006 | Maezawa et al. | |
| 6,997,923 B2 | 2/2006 | Anderson | |
| 7,006,874 B2 | 2/2006 | Knowlton | |
| 7,020,528 B2 | 3/2006 | Neev | |

(56) References Cited

U.S. PATENT DOCUMENTS

| | | |
|---|---|---|
| 7,022,089 B2 | 4/2006 | Ooba |
| 7,058,440 B2 | 6/2006 | Heuscher et al. |
| 7,063,666 B2 * | 6/2006 | Weng ............... A61B 17/0057 600/439 |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 * | 11/2007 | Trucco ............... G10K 11/34 600/443 |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton |
| 7,530,958 B2 | 5/2009 | Slayton |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,686,763 B2 | 3/2010 | Vaezy et al. |
| 7,695,437 B2 | 4/2010 | Quistgaard et al. |
| 7,758,524 B2 | 7/2010 | Barthe |
| 7,789,841 B2 | 9/2010 | Huckle et al. |
| 7,824,348 B2 * | 11/2010 | Barthe ............... A61N 7/00 600/437 |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 2001/0009997 A1 | 7/2001 | Pope |
| 2001/0009999 A1 | 7/2001 | Kaufman et al. |
| 2001/0014780 A1 | 8/2001 | Martin et al. |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton et al. |
| 2002/0095143 A1 | 7/2002 | Key |
| 2002/0099094 A1 | 7/2002 | Anderson |
| 2002/0115917 A1 | 8/2002 | Honda et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | Mchale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 * | 2/2003 | Slayton ............... A61B 5/01 600/439 |
| 2003/0040739 A1 | 2/2003 | Koop |
| 2003/0060736 A1 | 2/2003 | Martin et al. |
| 2003/0050678 A1 | 3/2003 | Sierra |
| 2003/0055417 A1 | 3/2003 | Truckai et al. |
| 2003/0040442 A1 | 4/2003 | Ishidera |
| 2003/0065313 A1 | 4/2003 | Koop |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 * | 7/2003 | Ustuner ............... A61B 8/00 600/459 |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |

(56) References Cited

U.S. PATENT DOCUMENTS

| | | |
|---|---|---|
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002705 A1 | 1/2004 | Knowlton |
| 2004/0010222 A1 | 1/2004 | Nunomura et al. |
| 2004/0015106 A1 | 1/2004 | Coleman |
| 2004/0030227 A1 | 2/2004 | Littrup |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishbashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste et al. |
| 2004/0267252 A1 | 12/2004 | Washington et al. |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1* | 3/2005 | Maki .................... A61N 7/02 607/2 |
| 2005/0074407 A1 | 4/2005 | Smith |
| 2005/0080469 A1 | 4/2005 | Larson |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin |
| 2006/0116583 A1 | 6/2006 | Ogasawara et al. |
| 2006/0116671 A1 | 6/2006 | Slayton |
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0229514 A1 | 10/2006 | Wiener |
| 2006/0241440 A1 | 10/2006 | Eshel |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0261584 A1 | 11/2006 | Eshel |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslaysky et al. |
| 2007/0219605 A1 | 9/2007 | Yaroslaysky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0027328 A1 | 1/2008 | Klopotek et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0097253 A1 | 4/2008 | Pederson |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294073 A1 | 11/2008 | Barthe et al. |
| 2008/0319356 A1 | 12/2008 | Cain et al. |

(56) References Cited

U.S. PATENT DOCUMENTS

| | | |
|---|---|---|
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | Debenedictis et al. |
| 2010/0011236 A1 | 1/2010 | Barthe et al. |
| 2010/0022919 A1 | 1/2010 | Peterson |
| 2010/0022922 A1 | 1/2010 | Barthe et al. |
| 2010/0042020 A1 | 2/2010 | Ben-Ezra |
| 2010/0049178 A1 | 2/2010 | Deem et al. |
| 2010/0063422 A1 | 3/2010 | Hynynen et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0280420 A1 | 11/2010 | Barthe et al. |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | Mccormack et al. |
| 2011/0112405 A1 | 5/2011 | Barthe et al. |
| 2011/0178444 A1 | 7/2011 | Slayton et al. |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe et al. |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin et al. |
| 2012/0197121 A1 | 8/2012 | Slayton et al. |
| 2012/0215105 A1 | 8/2012 | Slayton et al. |
| 2012/0271294 A1 | 10/2012 | Barthe et al. |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe et al. |
| 2012/0330223 A1 | 12/2012 | Makin et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018286 A1 | 1/2013 | Slayton et al. |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0096471 A1 | 4/2013 | Slayton et al. |
| 2013/0190659 A1 | 7/2013 | Slayton et al. |
| 2013/0211258 A1 | 8/2013 | Barthe et al. |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0303904 A1 | 11/2013 | Barthe et al. |
| 2013/0303905 A1 | 11/2013 | Barthe et al. |
| 2013/0310863 A1 | 11/2013 | Barthe et al. |
| 2014/0082907 A1 | 3/2014 | Barthe |
| 2014/0142430 A1 | 5/2014 | Slayton et al. |
| 2014/0148834 A1 | 5/2014 | Barthe et al. |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | |
|---|---|---|
| DE | 10219217 | 11/2003 |
| DE | 10219297 | 11/2003 |
| DE | 20314479 | 3/2004 |
| EP | 0344773 | 12/1989 |
| EP | 1479412 | 11/1991 |
| EP | 0473553 A | 3/1992 |
| EP | 0661029 A | 7/1995 |
| EP | 1050322 | 11/2000 |
| EP | 1234566 | 8/2002 |
| EP | 1262160 | 12/2002 |
| EP | 1374944 A | 1/2004 |
| GB | 2113099 | 8/1983 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7222782 | 8/1995 |
| JP | 09047458 | 2/1997 |
| JP | 11505440 | 5/1999 |
| JP | 11506636 | 6/1999 |
| JP | 2000166940 | 6/2000 |
| JP | 2001170068 | 6/2001 |
| JP | 2002078764 | 3/2002 |
| JP | 2002515786 | 5/2002 |
| JP | 2002521118 | 7/2002 |
| JP | 2002537939 | 11/2002 |
| JP | 2003050298 | 2/2003 |
| JP | 2003204982 | 7/2003 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2007505793 A | 3/2007 |
| JP | 2009518126 | 5/2009 |
| JP | 2010517695 | 5/2010 |
| KR | 1020010024871 | 3/2001 |
| KR | 100400870 B1 | 10/2003 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| WO | 9625888 | 8/1996 |
| WO | 9639079 A1 | 12/1996 |
| WO | 9735518 | 10/1997 |
| WO | 9832379 | 7/1998 |
| WO | 9933520 | 7/1999 |
| WO | 9949788 | 10/1999 |
| WO | 0006032 | 2/2000 |
| WO | 0015300 | 3/2000 |
| WO | 0021612 | 4/2000 |
| WO | 0053113 | 9/2000 |
| WO | 0128623 | 4/2001 |
| WO | 0182777 | 11/2001 |
| WO | 0182778 | 11/2001 |
| WO | 0187161 | 11/2001 |
| WO | 0209813 | 2/2002 |
| WO | 02024050 | 3/2002 |
| WO | 02092168 A | 11/2002 |
| WO | 020292168 | 11/2002 |

(56) References Cited

FOREIGN PATENT DOCUMENTS

| | | |
|---|---|---|
| WO | 03053266 A | 7/2003 |
| WO | 03065347 | 8/2003 |
| WO | 03070105 | 8/2003 |
| WO | 03077833 | 8/2003 |
| WO | 03086215 | 10/2003 |
| WO | 03096883 | 11/2003 |
| WO | 03099177 | 12/2003 |
| WO | 03101530 | 12/2003 |
| WO | 2004000116 A | 12/2003 |
| WO | 2004080147 | 9/2004 |
| WO | 2004110558 | 12/2004 |
| WO | 2005011804 A | 2/2005 |
| WO | 2005065408 | 7/2005 |
| WO | 2005090978 | 9/2005 |
| WO | 2006036870 | 4/2006 |
| WO | 2006042163 A | 4/2006 |
| WO | 2006042168 | 4/2006 |
| WO | 2006042201 | 4/2006 |
| WO | 2006065671 | 6/2006 |
| WO | 2006082573 | 8/2006 |
| WO | 2007067563 A | 6/2007 |
| WO | 2008024923 A2 | 2/2008 |
| WO | 2008036622 A | 3/2008 |
| WO | 2009013729 | 1/2009 |
| WO | 2009149390 A1 | 12/2009 |
| WO | 2014055708 A1 | 4/2014 |

OTHER PUBLICATIONS

European Patent Office, Examination Report, EP 07814933.3, dated Aug. 5, 2014, 5 pages.
European Patent Office, Examination Report, EP 05798870.1, dated Oct. 20, 2014, 5 pages.
European Patent Office, Examination Report, EP 10185100.4, dated Oct. 24, 2014, 4 pages.
European Patent Office, Examination Report, EP 10185112.9, dated Oct. 24, 2014, 5 pages.
European Patent Office, Examination Report, EP 10185117.8, dated Oct. 24, 2014, 5 pages.
European Patent Office, Examination Report, EP 10185120.2, dated Oct. 24, 2014, 4 pages.
Sanghvi, N.T., et al., "Transrectal Ablation of Prostate Tissue Using Focused Ultrasound," 1993 Ultrasonics Symposium, IEEE, pp. 1207-1210.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fiels," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Smith, Nadine Barrie, et al., "Non-Invasive In Vivo Temperature Mapping of Ultrasound Heating Using Magnetic Resonance Techniques", 1994 Ultrasonics Symposium, pp. 1829-1832, vol. 3.
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeFroce 7800 GT graphics processor Power MADD," http://techreport.com/reviews/2005q2/geforce-7800gtx/index.x?pg=1, Jun. 22, 2005, 4 pages.
White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.
Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Arthur et al., "Non-invasive estimation of hyperthermia temperatures with ultrasound," Int. J. Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Calderhead et al., One Mechanism Behind LED Photo-Therapy for Wound Healing and Skin Rejuvenation: Key Role of the Mast Cell, Laser Therapy, Jul. 2008, pp. 141-148, 17.3.
Chen, L. et al., ""Effect of Blood Perfusion on the ablation of liver perenchyma with high intensity focused ultrasound,"" Phys. Med. Biol; 38:1661-1673; 1993b.
Coon, Joshua et al., "Protein identification using sequential ion/ion reactions and tandem mass spectometry" Proceedings of the National Academy of Sciences of the USA, vol. 102, No. 27, Jul. 5, 2005, pp. 9463-9468.
European Examination Report in related Application No. 05808908.7 dated Jun. 29, 2009.
European Examination Report in related Application No. 05810308.6 dated Jun. 29, 2009.
European Examination Report in related Application No. 09835856.7 dated Apr. 11, 2004.
European Examination Report in related Application No. 10185100.4 dated Jan. 6, 2014.
European Examination Report in related Application No. 10185120.2 dated Jan. 22, 2014.
Corry, Peter M., et al., "Human Cancer Treatment with Ultrasound", IEEE Transactions on Sonics and Ultrasonics, vol. SU-31, No. 5, Sep. 1984, pp. 444,456.
Damianou et al., Application of the Thermal Dose Concept for Predicting the Necrosed Tissue Volume During Ultrasound Surgery,"" 1993 IEEE Ultrasound Symposium, pp. 1199-1202.
Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.
Davis, Brian J., et al., "An Acoustic Phase Shift Technique for the Non-Invasive Measurement of Temperature Changes in Tissues", 1985 Ultrasonics Symposium, pp. 921-924.
Decision of the Korean Intellectual Property Tribunal dated Jun. 28, 2013 regarding Korean Patent No. 10-1142108, wich is related to the pending application and/or application identified in the Table on the pages 2-5 of the information Disclosure Statement herein (English translation, English translation certification, and Korean decision included).
Fry, W.J. et al., "Production of Focal Destructive Lesions in the Central Nervous System with Ultrasound," J. Neurosurg., 11:471-478; 1954.
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9.
Harr, G.R. et al., "Tissue Destruction with Focused Ultrasound in Vivo," Eur. Urol. 23 (suppl. 1):8-11; 1993.

(56) References Cited

OTHER PUBLICATIONS

Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.

Hassan et al., "Structure and Morphology of Freeze/Thawed PVA Hydrogels," Macromolecules, Mar. 11, 2000, pp. 2472-2479, vol. 33, No. 7.

Husseini et al, "The Role of Cavitation in Acoustically Activated Drug Delivery," J. Control Release, Oct. 3, 2005, pp. 253-261, vol. 107(2).

Husseini et al. "Investigating the mechanism of accoustically activated uptake of drugs from Pluronic micelles," BMD Cancer 2002, 2:20k, Aug. 30, 2002, pp. 1-6.

International Search Report and Written Opinion dated Jan. 23, 2014 in Application No. PCT/US2012/046122.

International Search Report and Written Opinion dated Jan. 23, 2014 in Application No. PCT/US2012/046123.

International Search Report and Written Opinion dated Jan. 28, 2012 in Application No. PCT/US2012/046327.

International Search Report and Written Opinion dated Jan. 28, 2013 in Application No. PCT/US2012/046125.

International Search Report and Written Opinion dated Feb. 14, 2013 in Application No. PCT/US2011/001361.

International Search Report and Written Opinion dated Feb. 14, 2013 in Application No. PCT/US2011/001362.

International Search Report and Written Opinion dated Feb. 14, 2013 in Application No. PCT/US2011/001366.

International Search Report and Written Opinion dated Apr. 6, 2012 in Application No. PCT/US2011/001366.

International Search Report and Written Opinion dated Apr. 6, 2012 in Application No. PCT/US2011/001367.

Jeffers et al., "Evaluation of the Effect of Cavitation Activity on Drug-Ultrasound Synergisms," 1993 IEEE. Ultrasonics Symposium, pp. 925-928.

Jeffers et al., "Evaluation of the Effect of Cavitation Activity on Drug-Ultrasound Synergisms," 1993 IEEE Ultrasonics Symposium, pp. 925-928.

Jenne, J., et al., "Temperature Mapping for High Energy US-Therapy", 1994 Ultrasonics Symposium, pp. 1879-1882.

Johnson, S.A., et al., "Non-Intrusive Measurement of Microwave and Ultrasound-Induced Hyperthermia by Acoustic temperature Tomography", Ultrasonics Symposium Proceedings, pp. 977-982.

Madersbacher, S. et al., "Tissue Ablation in Bening Prostatic Hyperlasia with High Intensity Focused Ultrasound," Dur. Urol., 23, (suppl. 1):39-43;1993.

Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.

Makin et al, "Miniaturized Ultrasound Arrays for Interstitial Ablation and Imaging," UltraSound Med. Biol. 2005, Nov. 1, 2005, pp. 1539-1550, vol. 31(11).

Makin et al., "Confirmal Bulk Ablation and Therapy Monitoring Using Intracorporeal Image-Treat Ultrasound Arrays", 4th International Symposium on Therapeutic Ultrasound, Sep. 19, 2004.

Manohar et al, "Photoaccoustic mammography laboratory prototype: imaging of breast tissue phantoms," Journal of Biomedical Optics, Nov./Dec. 2004, pp. 1172-1181, vol. 9, No. 6.

Mast et al, "Bulk Ablation of Soft Tissue with Intense Ultrasound; Modeling nad Experiments," J. Acoust. Soc. Am., Oct. 1, 2005, pp. 2715-2724, vol. 118(4).

Mitragotri, Samir; "Healing sound: the use of ultrasound in drug delivery and other therapeutic applications," Nature Reviews; Drug Delivery, pp. 255-260, vol. 4.

Paradossi et al., "Poly(vinyl alcohol) as versatile biomaterial for potential biomedical applications," Journal of Materials Science: Materials in Medicine, 2003, pp. 687-691, vol. 14.

PCT/US2012/046122 International Search Report dated Jan. 30, 2013.

PCT/US2012/046123 International Search Report dated Jan. 28, 2013.

PCT/US2012/046125 International Search Report dated Jan. 28, 2013.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-Induced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

\* cited by examiner

ANNULAR ARRAY
(PLAIN VIEW)
PLANAR, FOCUSED
OR DEFOCUSED

SYSTEM AND METHOD FOR VARIABLE DEPTH ULTRASOUND TREATMENT

CROSS-REFERENCE TO RELATED APPLICATIONS

This application is a continuation of U.S. patent application Ser. No. 12/834,754 entitled "SYSTEM AND METHOD FOR VARIABLE DEPTH ULTRASOUND TREATMENT" filed on Jul. 12, 2010, issued as U.S. Pat. No. 8,708,915 on Apr. 29, 2014, which is a continuation of U.S. patent application Ser. No. 10/944,500 entitled "SYSTEM AND METHOD FOR VARIABLE DEPTH ULTRASOUND TREATMENT" filed on Sep. 16, 2004, issued as U.S. Pat. No. 7,824,348 on Nov. 2, 2010, all of which are incorporated herein by reference.

FIELD OF INVENTION

This invention generally relates to an ultrasound system, and more particularly, to a method and system for variable depth ultrasound treatment.

BACKGROUND OF THE INVENTION

Many conventional applications of therapeutic ultrasound have employed low frequency transducers. These transducers have operational frequencies that typically range from 500 kHz to 1.5 MHz. Such low frequency transducers are often preferred because they allow for acoustical energy to be focused deep into the body, without harming the overlying tissue structures.

A conventional application of noninvasive therapeutic ultrasound using a low frequency transducer is depicted in FIG. 1. A conventional therapeutic system 100 comprises a transducer 102 that uses low frequency energy to treat a deep treatment region 110. Deep treatment region 110 is located at a deep depth 106 below a superficial region 112, e.g., tissue layers and structures, and a subcutaneous region 114 of a patient. Deep depth 106 may range from several millimeters to 5-7 centimeters or more. Conventional system 100 cannot treat superficial regions 112 or subcutaneous regions 114 through use of low-frequency transducer 102, thus limiting the applications of such systems. For example, some cosmetic surgeries ma also need to provide treatment to superficial and/or subcutaneous, as well as deep treatment regions, thus eliminating the use of lower frequency transducers.

Another undesirable side effect of low-frequency therapy is that the acoustic energy must pass through intervening tissue layers before reaching the desired deep treatment area. The intervening layers tend to defocus the rays and absorb some of the acoustic energy. This causes the focal spot size to widen, making it difficult to control the location of the focal snot.

SUMMARY OF THE INVENTION

In accordance with various aspects of the present invention, a variable depth ultrasound treatment method and system are provided. An exemplary method and system comprise a variable depth transducer system configured for providing ultrasound treatment to more than one region of interest, such as between at least two of a deep treatment region of interest, a superficial region of interest, and/or a subcutaneous region of interest.

In accordance with various exemplary embodiments, a variable depth transducer system can be configured for spatial control, such as by changing the distance from an exemplary transducer to a reflecting surface, or changing the angles of energy focused or unfocused to the region of interest, and/or configured for temporal control, such as by controlling changes in the frequency, drive amplitude and tinting of the exemplary transducer. As a result, changes in the location of the treatment region, the shape and size and/or volume of the spot or region of interest, as well as the thermal conditions, can be dynamically controlled versus time.

In accordance with an exemplary embodiment of the present invention, the variable depth transducer can comprise a transduction element having a piezoelectrically active layer, matching layers and/or other materials for generating radiation or acoustical energy. The variable depth transducer may be configured to operate at moderate frequencies to provide variable depth treatment. For example, an exemplary variable depth transducer system can be configured for providing treatment to a superficial region of interest, and/or to a subcutaneous region of interest utilizing moderate frequencies below 20 MHz, such as within a range from approximately 750 kHz to 20 MHz, or higher frequencies of 35 MHz or more.

In accordance with another exemplary embodiment of the present invention, the transduction element may be configured with a variable depth element comprising one or more materials configured to allow for control and focusing/defocusing of the acoustic energy to more than one region of interest, such as between a deep treatment region of interest and a superficial region of interest, and/or a subcutaneous region of interest. The materials utilized for the variable depth element for control and focusing/defocusing may be configured in a variety of manners and shapes, such as substantially flat, curved, or other arrangements for bending reflecting and/or redirecting radiation and acoustical energy. In addition, the variable depth element may be configured within, or comprise a device coupled to, the transduction element in a variety of manners to provide for focusing/defocusing and control of the treatment energy.

In accordance with another exemplary embodiment of the present invention, an exemplary transducer may be configured to enable energy deposition not only proximate a fundamental frequency of a piezoelectric material within the transduction element, but also at harmonic frequencies of the material, above a fundamental frequency, as well as resonances below a fundamental frequency. These multiple resonances may be controlled and enabled through various focusing techniques and transducer structures, including the adding of matching layers and/or backing layers to shape the resonant characteristics of the transducer.

In accordance with another exemplary embodiment of the present invention, a variable depth acoustic transducer can also be configured for generating high acoustic power for treatment purposes. While also providing for good imaging capabilities. For example, to allow for the treatment spot size to be optimally controlled at various treatment depths, an exemplary embodiment of the present invention may comprise a transducer configured into an array of sub-elements, each sub-element configured for processing acoustic waves with a sufficient bandwidth for good axial resolution.

In accordance with another exemplary embodiment of the present invention, a variable depth transducer may be configured in a probe arrangement to provide treatment. The variable depth transducer may also be configured with various mechanical devices to allow for optimal treatment and therapy, for example to provide controlled positioning of the variable depth transducer, such as through a non-invasive configuration. Further, the variable depth transducer may also be configured for one-dimensional, two-dimensional and annular arrays, and/or for three-dimensional treatment applications.

In accordance with another aspect of the present invention, an exemplary variable depth treatment system and method may also be configured to provide therapeutic heating, cooling and/or imaging of a treatment region as well as acoustically monitoring the temperature profile or other tissue parameter monitoring of the treatment region and the general vicinity thereof. For example, in accordance with an exemplary embodiment, an exemplary variable depth system may be configured with a dynamic feedback arrangement based on monitoring of temperature or other tissue parameters, and/or based on imaging information to suitably adjust the spatial and/or temporal characteristics of the variable depth transducer.

BRIEF DESCRIPTION OF THE DRAWINGS

The subject matter of the invention is particularly pointed out and distinctly claimed in the concluding portion of the specification. The invention, however, both as to organization and method of operation, may best be understood by reference to the following description taken in conjunction with the claims and the accompanying drawing figures, in which like parts may be referred to by like numerals:

DETAILED DESCRIPTION

The present invention may be described herein in terms of various components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical or treatment contexts, and the exemplary embodiments relating to a variable depth ultrasound treatment as described herein are merely a few of the exemplary applications for the invention. For example, the principles, features and methods discussed may be applied to any medical or other tissue or treatment application.

Figure 1:
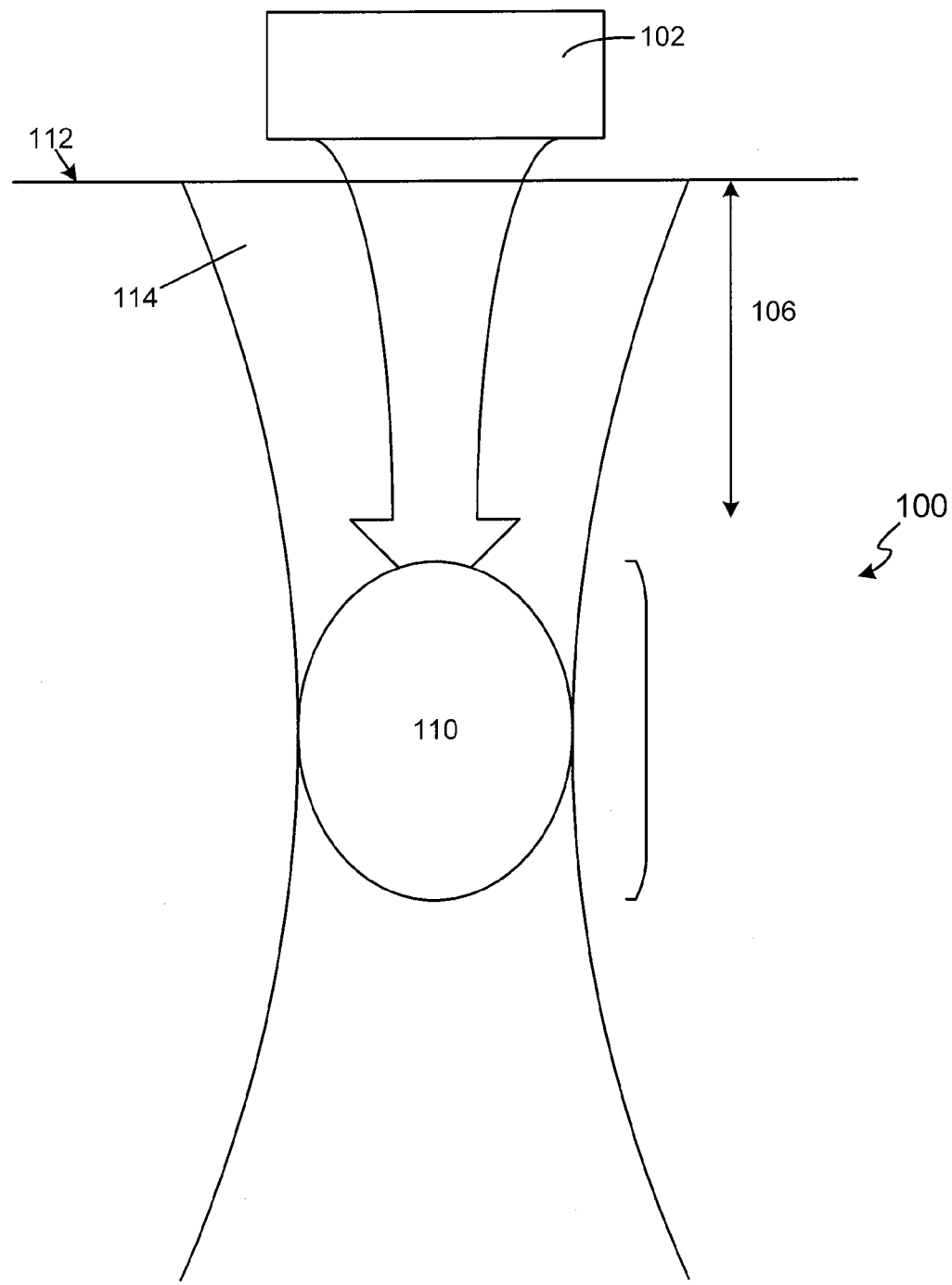
FIG. 1 illustrates a diagram of treatment using a prior art ultrasound treatment system.
Figure 2:
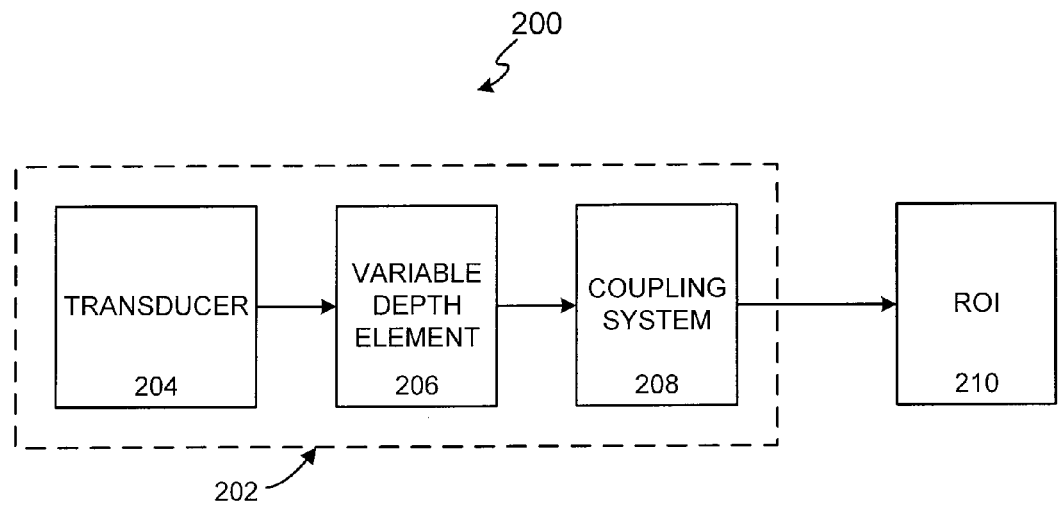
FIG. 2 illustrates a block diagram of an ultrasound treatment system in accordance with an exemplary embodiment of the present invention.

In accordance with various aspects of the present invention, a non-invasive variable depth ultrasound treatment method and system are provided. An exemplary method and system comprise a variable depth acoustic transducer system configured for providing ultrasound treatment to more than one region of interest in a patient. For example, with reference to an exemplary embodiment illustrated in a block diagram of FIG. 2, an exemplary system 200 for ultrasound treatment includes a variable depth transducer system 202 that provides treatment to a region of interest 210. Variable depth transducer system 202 may comprise a transducer 204 configured with a variable depth device 206. In providing treatment, variable depth ultrasound system 202 may provide therapy, imaging and/or temperature or other tissue parameter monitoring to region of interest 210. Region of interest 210 can comprise a deep treatment region, a superficial region, and/or a subcutaneous region of interest or any other region of interest located within a patient. To facilitate coupling of variable depth ultrasound system 202 to region of interest 210, variable depth ultrasound system 202 can further comprise a coupling system 208 configured for acoustic coupling of ultrasound energy and signals.

Figure 3:
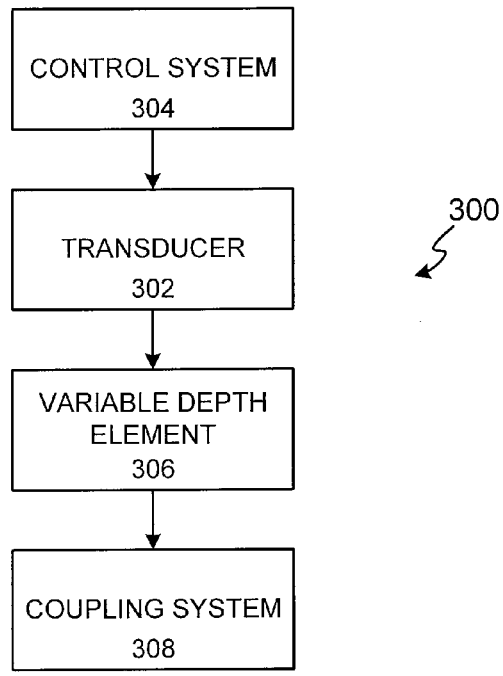
FIG. 3 illustrates a block diagram of a variable depth ultrasound treatment system in accordance with an exemplary embodiment of the present invention.

An exemplary variable depth transducer system 300 is further exemplified in a block diagram illustrated in FIG. 3. Variable depth transducer system 300 may comprise a control system 304, a transducer 302, a variable depth element 306, and a coupling system 308. Control system 304 is configured for control and operation of transducer 302 to provide treatment to more than one region of interest. Transducer 302 and variable depth device 306 are configured to provide variable depth ultrasound treatment to a treatment region. Coupling system 303 is configured for coupling of transducer 302 and variable depth device 306 to a region of interest.

Control system 304 may be configured for use within an ultrasound therapy system, an ultrasound imaging system, and/or an ultrasound imaging, therapy and/or treatment monitoring system, including motion control subsystems. In accordance with an exemplary embodiment, a control system 304 may comprise, a processor, a display, and/or one or more input devices. The processor may comprise a personal computer, a Unix system, or any other conventional processing unit. The display may comprise a monitor, LCD screen, or any other device configured to display an image. An input/output device ma comprise a keyboard, a mouse, a touch-screen, or any other device for inputting information. The information from the input device and images displayed may be received or transmitted in any format, such as manually, by analog device, by digital device, and/hr by any other mechanisms. The processor, display, and/of input device may be coupled together in any manner. By coupling, the devices comprising control system 304 may be directly connected to each other or may be connected through one or more other devices or components that allow a signal to travel to/from one component to another. The various coupling components for the devices comprising control system 304 can include but are not limited to the internet, a wireless network, it conventional wire cable, an optical cable or connection through any other medium that conducts signals, and any other coupling device or communication medium.

Coupling system 308 is configured for the coupling ultrasound energy and signals between transducer 302 and variable depth device 306 and a region of interest. Coupling system 308 may facilitate such coupling through use of various coupling mediums, including air and other gases, water and other fluids, gels, solids, and/or any combination thereof, or any other medium that allows for signals to be transmitted between transducer 302/variable depth device 306 and the region of interest. In addition to providing a coupling function, in accordance with an exemplary embodiment, coupling system 308 can also be configured for providing temperature control during the treatment application. For example, coupling system 308 can be configured for controlled cooling of an interface surface or region between transducer 302/variable depth device 306 and the region of interest by suitably controlling the temperature of the coupling medium. The suitable temperature for such coupling medium can be achieved in various manners, and utilize various feedback systems, such as thermocouples, thermistors or any other device or system configured for temperature measurement of a coupling medium. Such controlled cooling can be configured to further facilitate spatial control of variable depth transducer system 300.

Exemplary variable depth transducer 302 can be configured in various manners. For example, a variable depth transducer system can be configured for spatial control, such as by controlled changing of the distance from an exemplary transducer to a reflecting surface or controlled changing of the angles of energy focused or unfocused to the region of interest, e.g., variable depth transducer 302 can be configured with variable depth element 306 comprising a frequency dependent lens configured for control of focal depth and position by changing the frequency of excitation of variable depth transducer 302. In addition, variable depth transducer 302 can also be configured for temporal control, such as by controlling changes in the frequency, drive amplitude and timing of the exemplary transducer. Thus, an exemplary variable depth transducer can be configured with spatial and/or temporal control. As a result, changes in the location of the treatment region, the shape and size and/or volume of the spot or region of interest, as well as the thermal conditions, can be dynamically controlled versus time.

Variable depth element 306 can be suitably coupled to transducer 302 to facilitate variable depth treatment. By coupling, transducer 302 may be directly and/or movably connected to variable depth device 306, or may be connected through one or more various components or elements that enable energy and/or signals to travel to/from one component to another. Transducer 302 and variable depth element 306 may also be combined into a single device, wherein variable depth device 306 is configured within transducer 302 e.g., as a part of as transduction element of transducer 302.

Figure 4:
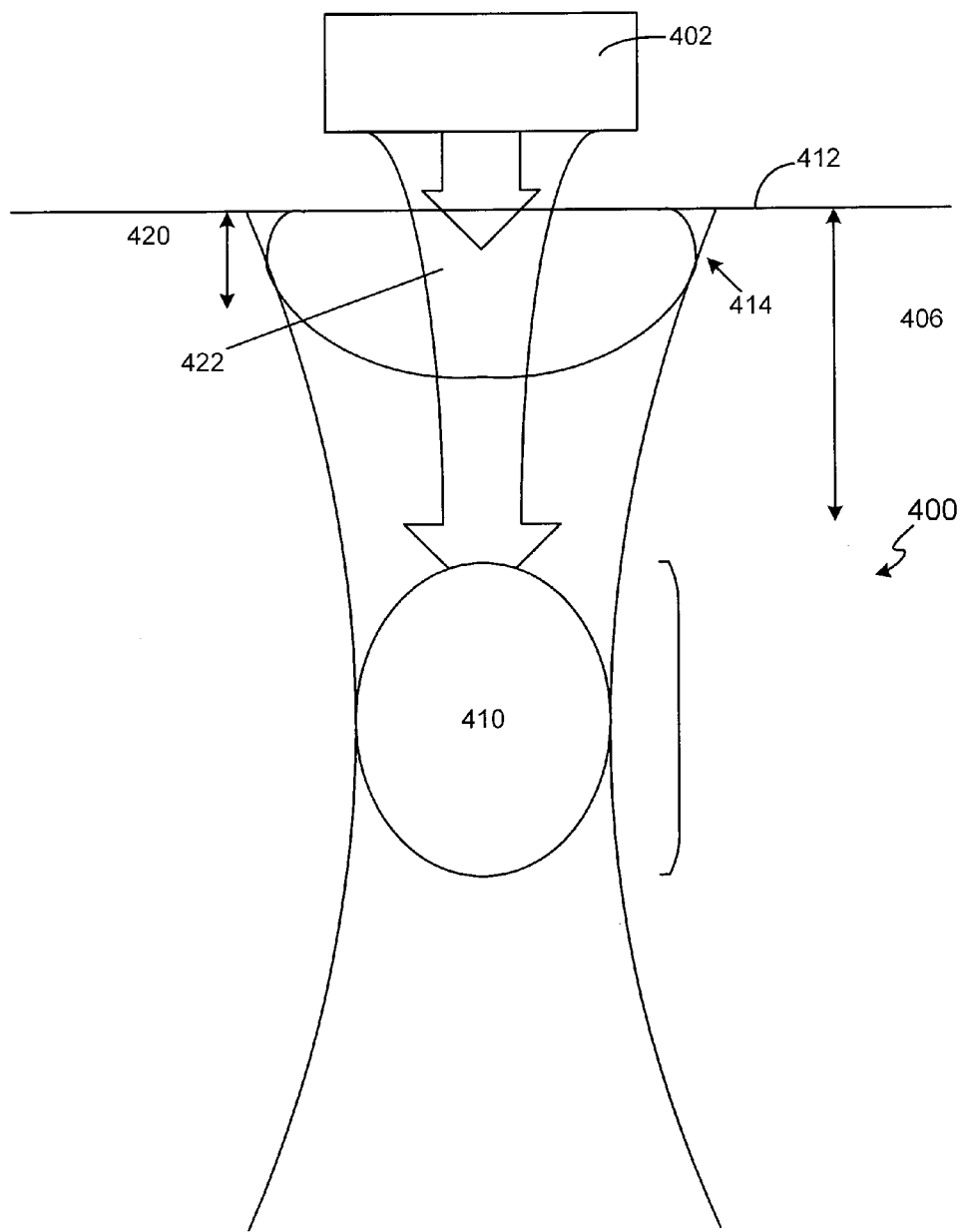
FIG. 4 illustrates a diagram of a variable depth ultrasound treatment system in accordance with an exemplary embodiment of the present invention.

Variable depth element 306 can configured to enable variable depth treatment system 300 to provide treatment to more than one region of interest, such as between a deep treatment region of interest, a superficial region of interest, and/or a subcutaneous region of interest, or other regions in between. Such treatment can occur within a single region of interest, or within more than one region of interest, at the same time. For example, with momentary reference to FIG. 4, an exemplary embodiment of a variable depth treatment system 400 is shown. Variable depth treatment system 400 may be configured for operating within moderate frequencies ranging from approximately 750 kHz to 20 MHz or more. Variable depth treatment system 400 may be configured with a variable depth transducer system 402 comprising a transducer configured, with a variable depth device. Variable depth transducer system 402 may be coupled to a control system for receiving and transmitting signals to/front a region of interest.

During operation, variable depth transducer system 402 may be configured to transmit or receive signals to treat a deep treatment region 410 located at deep depth 406 within a patient. For example, depth 406 for deep treatment region 410 may range from approximately 50 mm to 7 cm or more.

Variable depth transducer system 402 may also be configured to treat a second inner region 422 of a patient. Inner region 422 may comprise a superficial layer 412 of a patient and/or a subcutaneous layer 414 of patient. Inner region 422 is located at a shorter depth 420 within tissue layers of a patient. For example, depth 420 may range from approximately 0 mm to 5 cm or more within a patient, wherein the 0 mm range comprises the outer surface of superficial layer 412 of the patient. In other words, superficial layer 412 of the patient may comprise any area on or near the surface of the patient. Treatment by variable depth treatment system 400 may include treatment of both deep region 410 and inner region 422, or within only one region of interest.

Variable depth element 306 can be configured in various manners to facilitate treatment of more than one region of interest, such as inner region 422 and/or deep-seated region 410. In accordance with an exemplary embodiment of the present invention, transducer 302 may be configured with variable depth element 306 comprising one or more materials configured to allow for control and focusing/defocusing of the acoustic energy to more than one region of interest. For example, with reference to exemplary embodiments illustrated in FIGS. 5A and 5B, a variable depth transducer system 500 can comprise a transducer 502, electrical leads 510, and a variable depth device 528 or 530 suitably configured with transducer 502 to facilitate treatment.

Transducer 502 can include a transduction element comprising a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In addition to or instead of a piezoelectrically active material, variable depth transducer 502 may comprise any other materials configured for generating radiation and/or acoustical energy. Variable depth transducer 502 may also comprise one or more matching layers and/or backing layers to suitably shape the resonant character of transducer 502. For example, variable depth transducer 502 may be configured, along with transduction element, with one or more matching layers and/or backing layers coupled to a piezoelectrically active material or any other material configured for generating radiation and/or acoustical energy.

For temporal control, the thickness of the transduction element of variable depth transducer 502 may be selected to provide a center operating frequency of moderate range, for example from approximately 750 kHz to 30 MHz or more. Lower frequencies, e.g., between approximately 750 kHz and 8 MHz, can facilitate deeper penetration and higher frequencies, e.g., between approximately 8 to 20 MHz or more, can facilitate greater resolution. Selecting the frequency for operation can be based on the degree and balance of energy penetration and resolution that is desired for an application.

Electrical leads 510 may be configured to enable power to be transmitted to and signals received from variable depth transducer 502, and can comprise any wiring type, configuration and arrangement for use with ultrasound transducers. Variable depth transducer 502 may also be coupled to electrical leads 510 in various manners. For example, while FIG. 5 depicts electrical leads 510 coupled to only one end of variable depth transducer 502, electrical leads 510 may also be coupled together on an opposite end, or any other location along variable depth transducer 502.

To facilitate spatial control, in an exemplary embodiment, variable depth device 528 can comprise one or more reflective materials 504 configured to provide control and focusing of acoustic or radiation energy from variable depth transducer 502 towards a region of interest 518. In accordance with an exemplary embodiment, reflective materials 504 can comprise acoustic mirrors, lenses, reflectors or prisms configured far focusing of acoustic or radiation energy. The exemplary mirrors, reflectors or prisms may comprise any material for reflecting, bending or redirecting acoustic or radiated energy. For example, such materials may include stainless steel, aluminum, or any other metal, alloy, glass, plastic, or any other material capable of bending, redirecting and/or reflecting back acoustical energy from a surface to another direction.

In accordance with one exemplary embodiment, reflective materials 504 may be suitably inclined at approximately a 45 degree angle with respect to variable depth transducer 502; however, reflective materials 504 may be configured to be inclined at any angle with respect to variable depth transducer 502 such that energy transmitted from variable depth transducer 502 is bent, redirected or reflected from reflective materials 504 towards a region of interest 518. Changing the angle of inclination can suitably control the focusing of acoustic energy to any one region of interest 518, such as to a deep treatment region of interest, a superficial region of interest, or a subcutaneous region of interest.

Figure 5B:
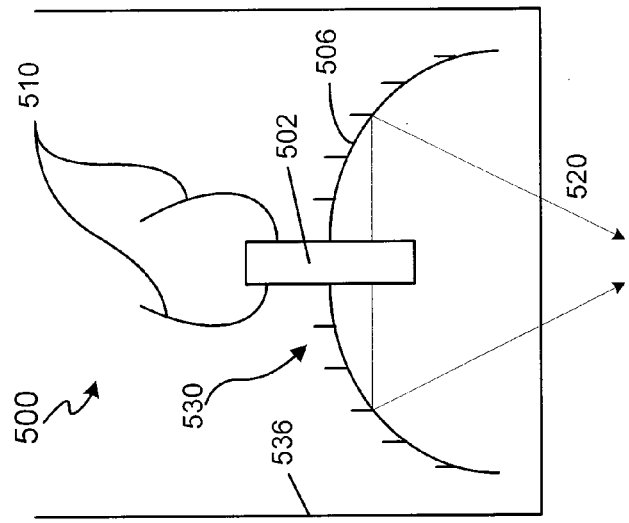
FIGS. 5A and 5B illustrate exemplary embodiments for variable depth ultrasound transducers for treatment in accordance with the present invention.

Variable depth devices 528 and 530 may be configured in a variety of manners, such as substantially flat, curved, or other suitable arrangements for reflecting, bending or redirecting acoustic or radiated energy. For example, with reference to FIG. 5A, variable, depth device 528 can comprise mirrors 504 configured in a substantially flat manner. However, with reference to FIG. 5B, variable depth device 530 can also comprise mirrors 506 configured in a curved arrangement to allow far focusing of energy from variable depth transducer 502 to a region of interest 520. While FIG. 5B illustrates mirrors 506 as substantially spherical and symmetric, mirrors 506 may also be curved in an aspherical and/or asymmetric manner such that energy transmitted from variable depth transducer 502 is bent, redirected, or reflected from mirrors 506 towards a region of interest 520. Still further, mirrors 506 can also be configured in other shapes and arrangements, such as jagged, saw tooth, wavy or other non-planar surfaces, or any other surface or compound surfaces configured for reflecting, bending or redirecting acoustic or radiated energy.

Figure 5A:
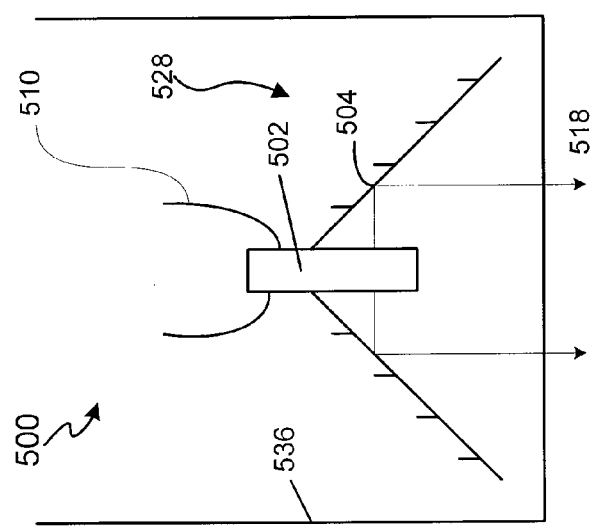

Moreover, while FIG. 5A depicts variable depth device 528 with mirrors 504 configured to be substantially flat, and FIG. 5B depicts variable depth device 530 with mirrors 506 configured to be curved, variable depth devices 528, 530 may also be configured with any combination of substantially flat, curved mirrors, and/or other planar, non-planar or other arrangements for facilitating spatial control. In accordance with an exemplary embodiment utilizing spatial and temporal control, variable depth devices 528 and 530 can be configured with a frequency dependent mirror or lens configured for spatial control of the focal depth and position by changing the frequency of excitation of variable depth transducer 502.

As a result, an exemplary transducer system 500 can be configured for providing treatment to a superficial region of interest and/or to a subcutaneous region of interest utilizing moderate frequencies below approximately 20 MHz. For example, an exemplary transducer system 500 can provide treatment to superficial regions and/or to subcutaneous regions that are more commonly addressed in cosmetic applications with an operating, frequency range from approximately 750 kHz to 35 MHz or more.

Variable depth transducer system 500 can be configured in various arrangements to provide non-invasive treatment. For example, in accordance with an exemplary embodiment, variable depth devices 528, 530 may be configured with variable depth transducer 502 within a housing 536. Housing 536 can comprise any configuration of transducer housing for containing transducers and for interfacing with a patient to allow treatment, such as facilitate noninvasive treatment. Coupling of signals from transducer 502 and variable depth devices 528, 530 through housing 536 to a region of interest may be facilitated through any coupling medium, such as air and other gases, water and other fluids, gels, solids, any combination thereof, and/or any other medium that allows for signals to be transmitted from transducer 502/variable depth devices 528, 530 to a region of interest.

In addition to comprising separate devices and components, variable depth transducer 302 and variable depth element 306 may also comprise the same device, i.e., variable depth element 306 is configured within transducer 302. For example, with reference to an exemplary embodiment illustrated in FIG. 6, a variable depth transducer system 600 can comprise a variable depth transducer 602 configured as a variable depth device to provide for control and focusing of acoustic energy 620 towards a region of interest 630.

Variable depth transducer 602 may comprise a transduction element comprised of a piezoelectrically active material, such as lead zirconante titanate (PZT), or any other piezoelectrically active material, such as a piezoelectric ceramic, crystal, plastic, and/or composite materials, as well as lithium niobate, lead titanate, barium titante, and/or lead metaniobate. Variable depth transducer 602 may also comprise one or more matching and/or backing layers configured along with the piezoelectrically active material. In addition to or instead of a piezoelectrically active material, variable depth transducer 602 may comprise any other materials configured for generating radiation and/or acoustical energy.

In accordance with an exemplary embodiment, variable depth transducer 602 is configured in a curved manner to enable focusing of acoustic energy 620 to region of interest 630. The curvature can be substantially spherical and/or symmetric manner, or curved in an aspherical and/or asymmetric manner. Furthermore, variable depth transducer 602 can comprise any other configuration to enable focusing of acoustic energy 620 to region of interest 630, such as to a deep treatment region of interest, a superficial region of interest, and/or a subcutaneous region of interest. For example, variable depth transducer 602 can be configured in an planar or non-planar arrangement.

For temporal control, the thickness of the transduction element of variable depth transducer 602 may be selected to provide a center operating frequency of moderate range, for example from approximately 750 kHz to 20 MHz. Lower frequencies, e.g., between approximately 750 kHz and 8 MHz, can facilitate deeper penetration and higher frequencies, e.g. between, approximately 8 to 30 MHz or more, facilitate greater resolution. As a result, an exemplary transducer system 600 can be configured for providing treatment to a superficial region of interest and/or to a subcutaneous region of interest utilizing moderate frequencies below 20 MHz. For example, an exemplar transducer system 600 can provide treatment to superficial regions and/or to subcutaneous regions that are more commonly addressed in cosmetic applications with an operating frequency range from approximately 750 kHz to 1.5 MHz or more.

Figure 6:
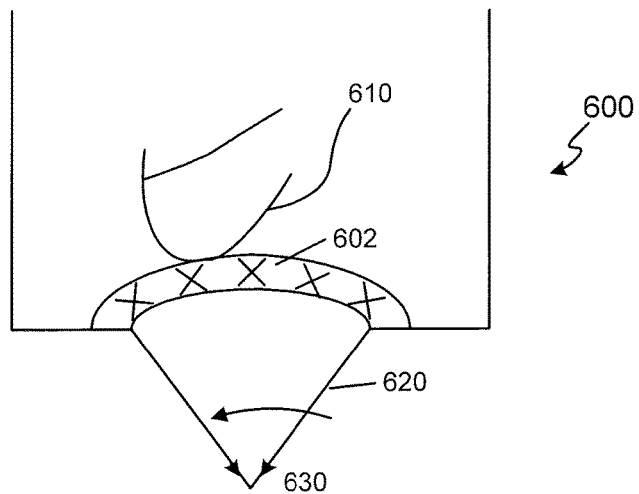
FIG. 6 illustrates another exemplary embodiment for a variable depth ultrasound transducer for treatment in accordance with the present invention.

Electrical leads 610 are configured to enable power to be transmitted to and signals received from variable depth transducer 602, and can comprise any wiring type, configuration and arrangement for use with ultrasound transducers. Variable depth transducer 602 may also be coupled to electrical leads 610 in various manners. For example, while FIG. 6 depicts electrical leads 610 coupled to only one side of variable depth transducer 602, electrical leads 610 may also be coupled together on an opposite end, or any other location along variable depth transducer 602.

Figure 7:
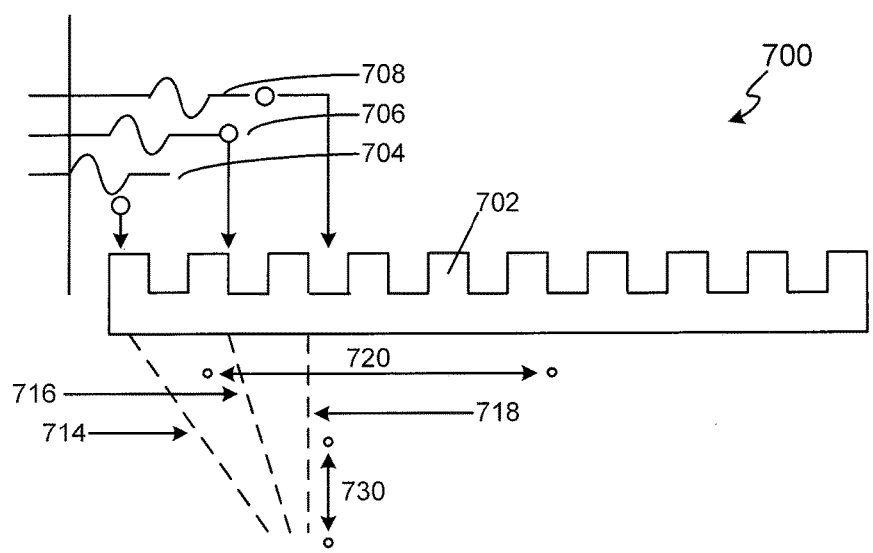
FIG. 7 illustrates an exemplary embodiment for electronic focusing of a transducer in accordance with the present invention.

In addition to having a variable depth transducer 602 configured as a variable depth device to provide for control and focusing of acoustic energy 620 towards a region of interest 630, in accordance with an exemplary embodiment, a variable depth transducer may also be configured electronically to provide for control and focusing of acoustic energy. For example, with reference to an exemplary embodiment depicted in FIG. 7, an exemplary electronic focusing transducer system 700 is illustrated. Electronic focusing transducer system 700 is configured with a variable depth transducer 702. Like transducers 502 and 602, variable depth transducer 702 may comprise a piezoelectrically active material, composite materials, one or more matching layers, and/or any other materials configured for generating, radiation and/or acoustical energy. Variable depth transducer 702 may also comprise a one-dimensional or two dimensional array of transducers.

In accordance with an exemplary embodiment, variable depth transducer 702 comprises one or more transducers and/or transduction elements that can be activated by various drive frequencies with suitable phase delay. For example, variable depth transducer 702 can be activated by a first drive frequency 704, and then subsequently activated by at least one or more delayed drive frequencies 706 or 708. The phase delay in drive frequencies allows for focusing of acoustical energy to occur both tangentially 720 and axially 730.

The drive frequencies 704, 706, 708 transmitted to variable depth transducer 702 may comprise substantially similar frequencies and/or different frequencies, wherein all frequencies are in the moderate range, i.e., between approximately 750 kHz to 20 MHz. The delay between drive frequencies 704, 706, 708 may range from 0 ms to approximately a full period or the drive frequency. For example, the delay may comprise zero or approximately $1/1000$th of a drive frequency period up to $15/16.\text{sup.th}$, $31/32.\text{sup.nd}$ or more of a drive frequency period, with variations comprising any fraction of a full wavelength in time delay.

Electronic phase delay focusing of variable depth transducer 702 may be done tangentially and/or axially. For example, drive frequencies 704, 706, 708 and/or the phase associated with drive frequencies 704, 706, 708 may be varied to provide focusing tangentially and/or axially. In accordance with an exemplary embodiment, variable depth transducer 702 may comprise subapertures that may be turned on and off to also provide focusing tangentially and/or axially. Phased focusing may prevent over-treatment of a region of interest by automating the focus and treatment times for a treatment region. Thus, for example, electronic control of variable depth transducer 702 may be facilitated by shunting various subapertures together to control the effective acoustic size of the source/receiver.

Thus, an exemplary transducer system can comprise a variable depth transducer 502, 602, 702 or any other transducer configuration for providing control and focus of acoustical and radiation energy to more than one region of interest within a patient. Such an exemplary transducer system can comprise a transducer configured with or coupled to a variable depth device or feature to provide energy to more than one region of interest. Moreover, an exemplary transducer system can provide treatment to superficial regions and/or to subcutaneous regions that are more commonly addressed in cosmetic applications with an operating frequency range below 30 MHz, or more, even from approximately 750 kHz to 8 MHz that is not attainable by prior art low-frequency transducers.

In accordance with another aspect of the present invention, a variable depth acoustic transducer can also be configured for generating high acoustic power for treatment purposes, while also providing for good imaging capabilities. To allow for the treatment spot size to be optimally controlled at various treatment depths, an exemplary embodiment of the present invention may comprise a transducer configured into an array of sub-elements.

For example, in accordance with an exemplary embodiment with reference again to FIG. 6, variable depth transducer 602 can comprise a plurality of sub-transduction elements, wherein any of the plurality of sub-transduction elements may be configured to provide for focusing energy 620, e.g., any of the plurality of sub-transduction elements can be configured for processing acoustic waves with a sufficient bandwidth for good axial resolution. The sub-transduction elements may be configured such that all are curved, e.g., with the same or varying curvatures, or with one or more sub-transduction elements being substantially flat, with the remaining sub-transduction elements being curved. Further, the sub-transduction elements can be configured in any other shapes configured to provide for control and focusing of acoustic energy 620 towards a region of interest 630.

In accordance with another exemplary embodiment of the present invention, an exemplary variable depth transducer system 300 may be configured to enable energy deposition not only proximate a fundamental frequency of a piezoelectric material within the transduction element, but also at other frequencies, such as harmonic frequencies of the material, above a fundamental frequency, as well as resonances below a fundamental frequency. These harmonic and below fundamental resonances may be controlled and enabled through various focusing techniques and transducer structures, including the adding of matching layers and/or backing layers to shape the resonant characteristics of the transducer.

For example, energy can be suitably provided to a treatment region at a frequency near the peak acoustic output or peak acoustic transmit efficiency of transducer 302 when a piezoelectrically active material is driven near its fundamental frequency. Different sized and shaped piezoelectric materials have different fundamental frequencies for various electrode configurations. In accordance with an exemplary embodiment, energy can also be deposited when the piezoelectric material is driven above its fundamental frequency, e.g., at harmonics, or when driven below the fundamental frequency. The use of the multiple frequency characteristics of transducer 302 may be controlled and enabled through various transducer configurations, acoustic control and/or focusing techniques.

Figure 8:
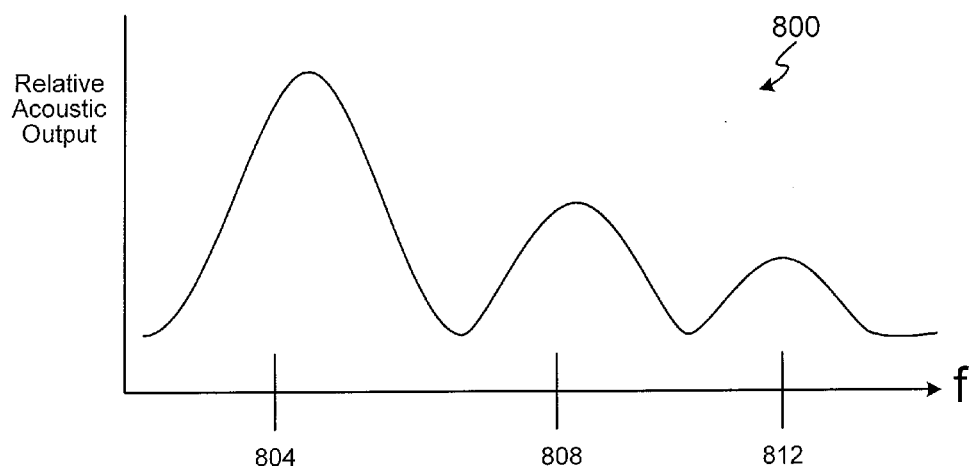
FIG. 8 illustrates an exemplary diagram of treatment characteristics of an exemplary transducer operating at the fundamental frequency and other frequencies and/or resonances above and below the fundamental in accordance with the present invention.

In accordance with an exemplary embodiment, the multiple frequencies may be enabled through the concentration of acoustic energy through the variable depth device 306. Enablement of the multiple frequencies allows for treatment at various depths corresponding to the different frequencies. For example, with additional reference to the acoustic output versus frequency curve illustrated in FIG. 8, variable depth transducer system 300 may treat multiple regions, represented by curve 800. Driving moderate frequencies through transducer 302 and variable depth device 306 may enable treatment of a first deep region 804, treatment of a second shallower region 808, and treatment of a third inner region 812. With respect to treatment techniques, various therapy, imaging and/or temperature monitoring applications may be provided to regions 804, 808, and/or 812. While three treatment regions are depicted in FIG. 8, variable depth transducer system 300 may be configured to enable multiple frequencies for treatment of two, four, or more regions.

In accordance with another aspect of the invention, the variable depth transducer 302 may be configured to provide one, two or three-dimensional treatment applications for focusing acoustic energy to one or more regions of interest. For example, as discussed above, variable depth transducer 302 can be suitably diced to form a one-dimensional array, e.g., transducer 602 comprising a single array of subtransduction elements.

Figure 9:
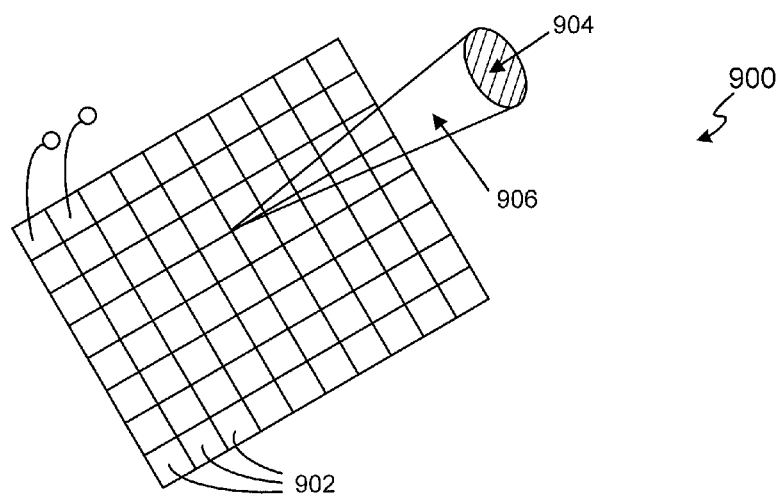
FIG. 9 illustrates an exemplary embodiment of a two-dimensional array in accordance with the present invention.

In accordance with another exemplary embodiment, variable depth transducer 302 may be suitably diced in two-dimensions to form a two-dimensional array. For example, with reference to FIG. 9, an exemplary two-dimensional array 900 can be suitably diced into a plurality of two-dimensional portions 902. Two-dimensional portions 902 can be suitably configured to focus on the treatment region at a certain depth, and thus provide respective slices 904 of the treatment region. As a result, the two-dimensional array 900 can provide a two-dimensional slicing of the image place of a treatment region, thus providing two-dimensional treatment.

In accordance with another exemplary embodiment, variable depth transducer 302 may be suitably configured to provide three-dimensional treatment. For example, to provide-three dimensional treatment of a region of interest, with reference again to FIG. 3, a three-dimensional system can comprise variable depth transducer 302 configured with an adaptive algorithm, such as, for example, one utilizing three-dimensional graphic software, contained in a control system, such as control system 304. The adaptive algorithm is suitably configured to receive two-dimensional imaging, temperature and/or treatment information relating to the region of interest, process the received information, and then provide corresponding three-dimensional imaging, temperature and/or treatment information.

In accordance with an exemplary embodiment, with reference again to FIG. 9, an exemplary three-dimensional system can comprise a two-dimensional array 900 configured with an adaptive algorithm to suitably receive 904 slices from different image planes of the treatment region, process the received information, and then provide volumetric information 906, e.g., three-dimensional imaging, temperature and/or treatment information. Moreover, after processing the received information with the adaptive algorithm, the two-dimensional array 900 may suitably provide therapeutic heating to the volumetric region 906 as desired.

Alternatively, rather than utilizing an adaptive algorithm, such as three-dimensional software, to provide three-dimensional imaging and/or temperature information, an exemplary three-dimensional system can comprise a single variable depth transducer 302 configured within a probe arrangement to operate from various rotational and/or translational positions relative to a target region.

Figure 10:
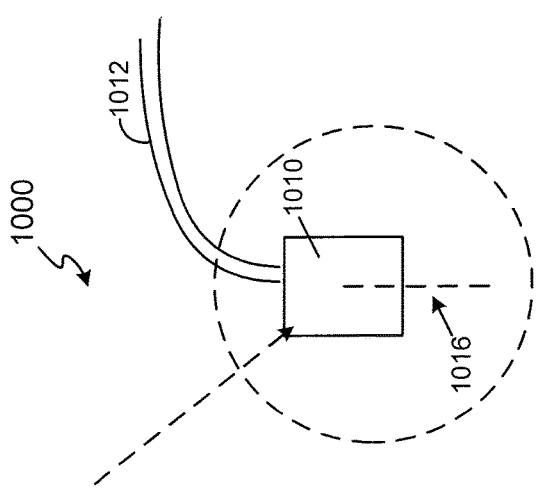
FIG. 10 illustrates an exemplary embodiment of a probe format for treatment in accordance with the present invention.

For example, with reference to FIG. 10, a probe 1010 can be configured to rotate around a perimeter of a treatment region 1014 to provide three-dimensional imaging and temperature information. Probe 1010 may comprise a variable depth transducer system, such as, for example with reference to FIG. 3, variable depth transducer 302 configured with variable depth device 306. In the exemplary embodiment, probe 1010 may be coupled to control system 304 through connector 1012. Connector 1012 may compose a wire, optical cable, wireless connection, or any other device capable of sending and/or receiving information from control system 304 to variable depth transducer 302 and variable depth device 306 housed within probe 100.

Probe 1010 may be configured to rotate around an axis 1016 to provide three-dimensional information. The rotational movement can comprise movement in either a clockwise or counterclockwise direction, or both. Further, the rotational movement could include complete or partial rotations. Thus, the rotational movement could include movement between only two positions, or between any other number of rotational positions. Still further, probe 1010 can be configured to translate or sweep along axis 1016 to provide a larger field-of-view and this facilitate additional three-dimensional information. Accordingly, the probe system 1000 may comprise rotational and/or translational movement suitably configured to provide three-dimensional information.

Figure 11:
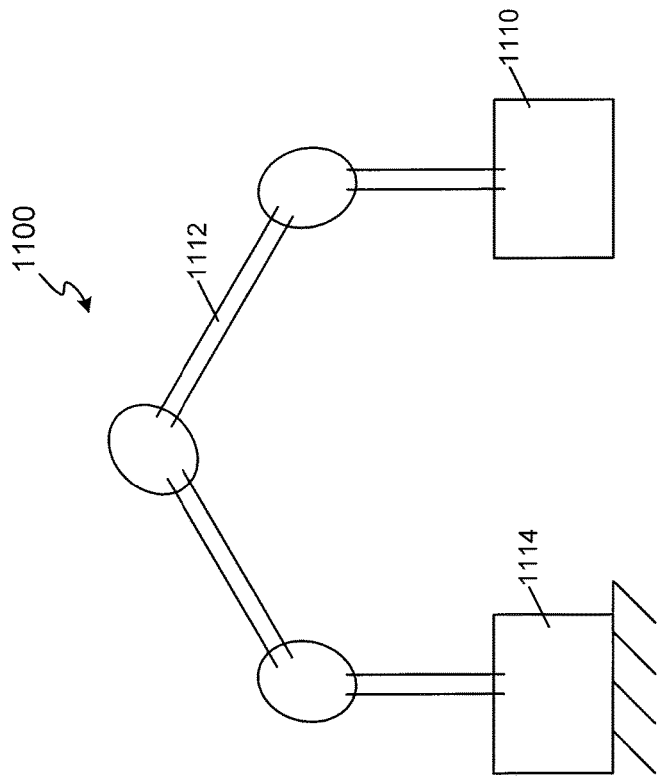
FIG. 11 illustrates an exemplary embodiment of a mechanism for treatment in accordance with the present invention.

Rotational and/or translational movement of probe 1010 may be controlled by maximally placing probe 100 in various desired rotational positions around the treatment region 1014. The movement of variable depth transducer 302 within probe 1010 in various rotational and/or translational positions can also be controlled by any mechanical scanning device now known or hereinafter devised for automated movement. For example, with reference to an exemplary embodiment illustrated in FIG. 11, automated rotational and/or translational movement may be achieved through use of a robotic arm mechanism 1100. Robotic arm mechanism 1100 comprises a manually and/or electromechanically actuated robotic arm 1112 coupled with a probe 1110 and a control 1114.

Probe 1110 may comprise a variable depth transducer system, such as variable depth transducer 302 configured with variable depth device 306. Movement of probe 1110 is mechanically provided through the operation of robotic arm 1112. Robotic arm 1112 may comprise one or more subsegments that allow precise movement and precise measurement of position in one or more up to any direction. Robotic arm 1112 may be driven by control system 1114. Control system 1114 may comprise a drive box, gears or any other device for providing mechanical movement of robotic arm 1112. Control system 1114 may also comprise a processor, a display, and/or an input/output device. Probe 1110 may be further coupled to control system 1114 through a wire or optical cable configured alongside or within robotic arm 1112, a wireless connection, or any other device capable of sending and/or receiving information from control system 1114 to variable depth transducer 302 and variable depth device 306 housed within niche 1110.

Control system 1114 may provide movement and control of robotic arm 1112 with up to six degrees of freedom. Control system 1114 rosy allow fin movement of robotic arm 1112 to be referenced with one or more fixed positions in space. Control system 1114 may also allow for movement of robotic arm 1112 to be referenced with one or more fixed positions on a patient.

While the three-dimensional systems may include a single acoustic transducer configured with a two-dimensional array 900 and an adaptive algorithm to provide three-dimensional imaging, temperature monitoring and therapeutic heating to a treatment region; the three-dimensional system may also be configured to include both an adaptive algorithm and rotational and/or translational movement to provide additional information. As such, an even larger area of treatment may be obtained through the use of both the adaptive algorithm and the rotational and/or translational movement.

Continuing with this example, the three-dimensional system can be suitably configured to capture imaging and temperature information and provide therapeutic heating from variable depth transducer 302 once variable depth transducer 302 becomes fixedly maintained at various rotational positions. The three-dimensional system can also be suitably configured to capture imaging and temperature information and provide therapeutic heating just prior to, or just after, becoming fixedly positioned. The three-dimensional system can also be configured to capture imaging and temperature information and provide therapy during movement around the various rotational positions.

Figure 12A:
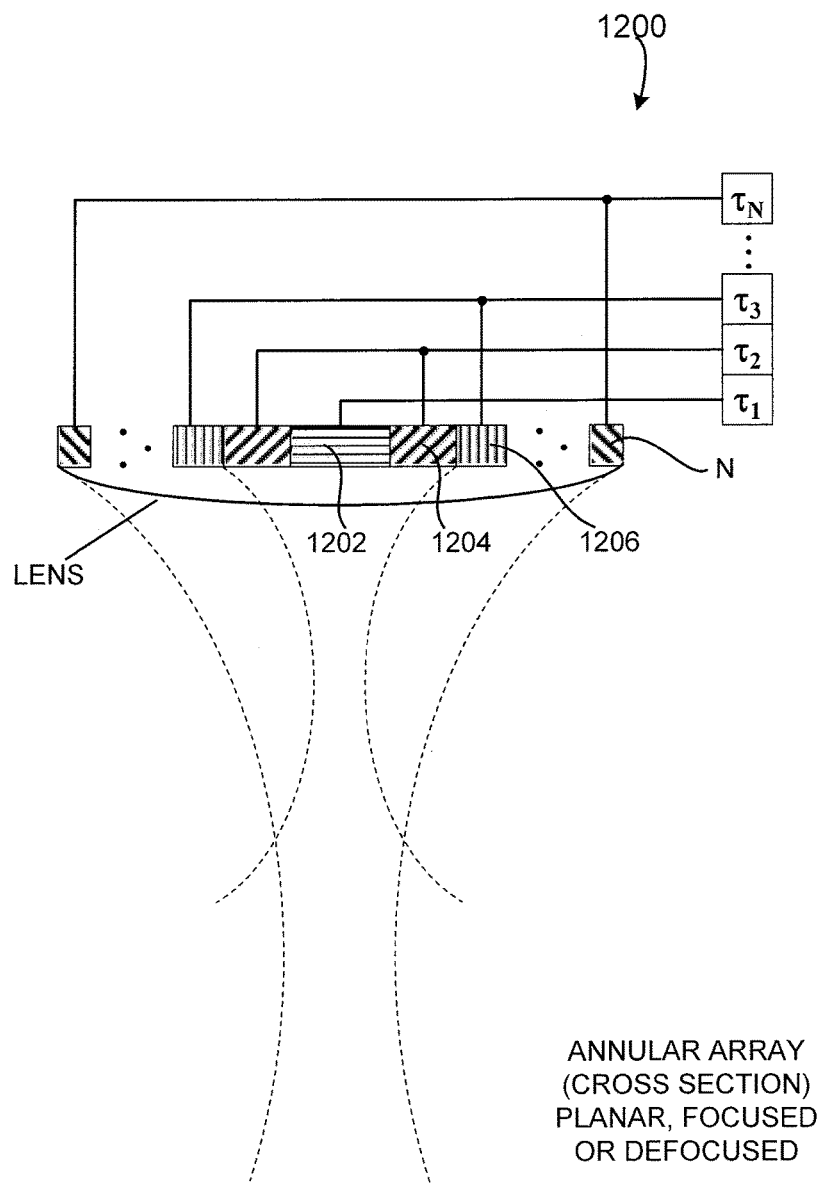
FIGS. 12A and 12B illustrate an exemplary embodiment of an annular array in accordance with the present invention.
Figure 12B:
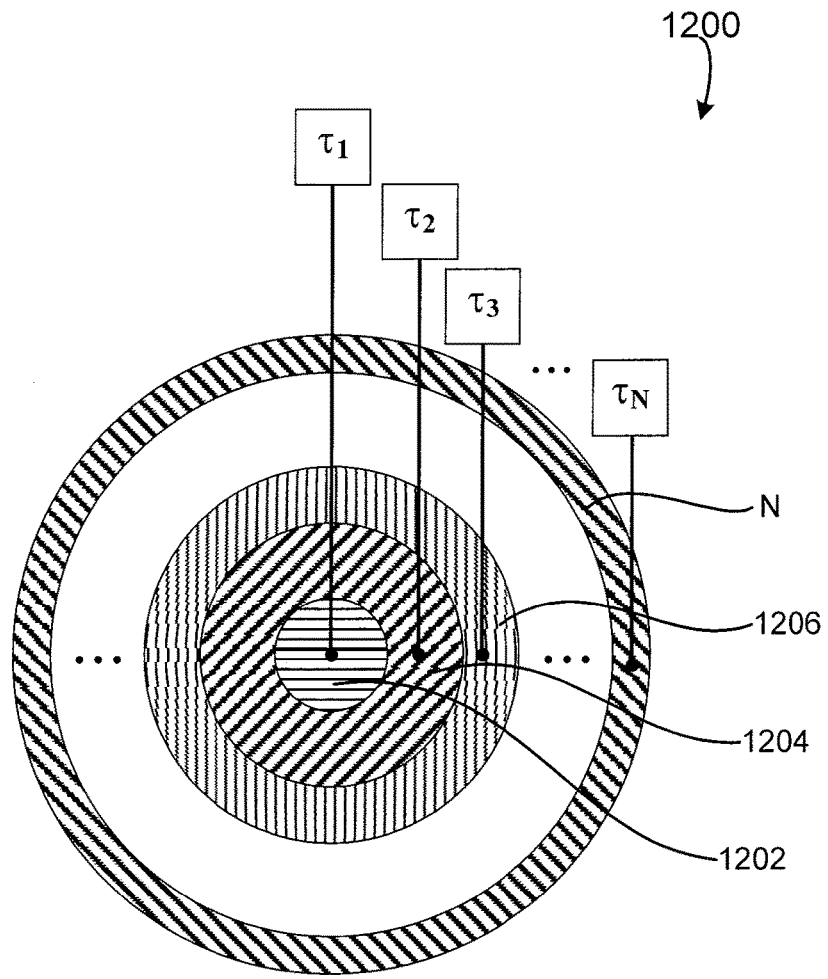

In addition to one, two or three-dimensional arrays, an exemplary variable depth transducer can also be configured within an annular array to provide planar, focused and/or defocused acoustical energy to more than one region of interest. For example, in accordance with an exemplary embodiment, with reference to FIGS. 12A and 12B, an annular array 1200 comprising a plurality of rings 1202, 1204, 1206 to N. Rings 1202, 1204, 1206 to N can be mechanically and electrically isolated into a set of individual elements, and can create planar, focused, or defocused waves. For example, such waves can be centered on-axis, such as by methods of adjusting corresponding transmit anther receive delays $\tau_1, \tau_2, \tau_3, \ldots \tau_n$. An electronic focus can be suitably moved along various depth positions, and can enable variable strength or beam tightness, while an electronic defocus can have varying amounts of defocusing. In accordance with an exemplary embodiment, a lens can also be provided to aid focusing or defocusing such that any time differential delays can be reduced. Movement of annular array 1200 in one, two or three-dimensions, or along any path, such as through use of probe 1000 and/or robotic arm mechanism 1100, may be implemented to scan and/or treat a volume or any corresponding space within a region of interest.

In accordance with another exemplary embodiment of the present invention, exemplary variable depth treatment system and method may also be configured to provide therapeutic heating, cooling and/or imaging of a treatment region as well as acoustically monitoring the temperature profile or other tissue parameter monitoring of the treatment region and the general vicinity thereof. In accordance with an exemplary embodiment, an exemplary variable depth system may be configured with a dynamic feedback arrangement based on monitoring of temperature or other tissue parameters, and/or based on imaging information to suitably adjust the spatial and/or temporal characteristics of the variable depth transducer. Such imaging and other temperature or tissue parameter information can be suitably collected from ultrasound signals transmitted from an exemplary variable depth transducer, or from separate devices configured for collecting such information, e.g., a laser device configured with a receiver for profiling temperature, imaging or other such information.

For example, with reference again to FIG. 4, such feedback information can be utilized to dynamically adjust the height, e.g., with a standoff, or distance of a transduction element within variable depth transducer system 402 from superficial layer 412. Such adjustment of the distance and/or location of variable depth transducer system 402 can be controlled either manually of mechanically. Changing the distance of variable depth transducer system 402 can result in a change in the depth of penetration of the acoustical energy within a region of interest, for example, from an inner region 422 to a deep region 410. The depth of penetration of the acoustical energy can also be suitably changed by changing the temperature of any couplant configured between variable depth transducer system 402 from superficial layer 412, and/or the temperature of any coolant.

Feedback information may be suitably generated or provided by any one or more acoustical sources, such as B-scan images, A-lines, Doppler or color flow images, surface acoustic wave devices, hydrophones, elasticity measurement, or shear wave based devices. In addition, optical sources can also be utilized, such as video and/or infrared cameras, laser Doppler imagers, optical coherence tomography hungers, and temperature sensors. Further, feedback information can also be suitably provided by semiconductors, such as thermistors or solid state temperature sensors, by electronic and electromagnetic sensors, such as impedance and capacitance measurement devices and/or thermocouples, and by mechanical sensors, such as stiffness gages, strain gages or stress measurement sensors, or any suitably combination thereof. Moreover, various other switches, acoustic or other sensing mechanisms and methods may be suitably employed to enable transducer 402 to be acoustically coupled to one or more regions of interest.

The present invention has been described above with reference to various exemplary embodiments. However those skilled in the art will recognize that changes and modifications may be made to the exemplary embodiments without departing from the scope of the present invention. For example, the various operational steps, as well as the components for carrying out the operational steps, may be implemented in alternate ways depending upon the particular application or in consideration of any number of cost functions associated with the operation of the system, e.g. various of the steps may be deleted, modified, or combined with other steps. Further, it should be noted that while the method and system for ultrasound treatment with a variable depth transducer as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, an exemplary variable depth transducer system can also be configured for at least some level of invasive treatment application. These and other changes or modifications are intended to be included within the scope of the present invention, as set forth in the following claims.

The invention claimed is:

1. A non-invasive ultrasound treatment system for providing treatment to a patient, the system comprising:
a variable depth transducer system comprising: a transducer having a surface and comprising at least one transduction element, and a variable depth element comprising a reflective surface, wherein:
the variable depth transducer system operable to provide treatment to a region of interest between a superficial and subcutaneous region of a patient, and
the reflective surface is configured to be inclined at any angle with respect to the transducer such that energy emitted by the surface of the transducer is bent, redirected or reflected from the reflective surface towards the region of interest;
wherein the variable depth transducer comprises a spatial control operable to change the angle of inclination of the reflective surface to focus the energy emitted by the surface of the transducer to any depth in the region of interest; and
a controller in communication with the transducer and the variable depth element, the controller comprising a control of the spatial control and a control of a frequency of the energy.

2. A non-invasive ultrasound treatment system for providing treatment to a patient, the system comprising:
a variable depth transducer system comprising:
a transducer having a surface and comprising at least one transduction element; and
a variable depth element comprising a reflective surface and a spatial control, the reflective surface configured to be inclined at an angle with respect to the transducer such that energy emitted by the surface of the transducer is bent, redirected or reflected from the reflective surface towards the region of interest, the spatial control configured to adjust the angle; and
a controller in communication with the transducer and the variable depth element, the controller configured to direct the spatial control to change the angle of inclination of the reflective surface to direct the energy emitted from the surface of the transducer to a predetermined depth in the region of interest and to adjust a frequency of the energy.

3. The non-invasive ultrasound treatment system according to claim 2, wherein the variable depth transducer is configured for variable control of the energy to change a depth location for a lesion created with the region of interest.

4. The non-invasive ultrasound treatment system according to claim 2 further comprising a coupling system configured for acoustic coupling between the variable depth transducer system and the region of interest.

5. The non-invasive ultrasound treatment system according to claim 4 wherein the coupling system is configured fix temperature control of the transducer to facilitate adjustment of a focal depth of the energy emitted by the surface of the transducer.

6. The non-invasive ultrasound treatment system according to claim 2, further comprising a mechanical scanning device configured to move the variable depth transducer system in at least one of a translational movement and a rotational movement.

7. The non-invasive ultrasound treatment system according to claim 2 wherein the variable depth transducer system is configured to image the region of interest.

8. The non-invasive ultrasound treatment system according to claim 2, wherein the frequency of the energy is in a range of 750 kHz to 20 MHz.

9. The non-invasive ultrasound treatment system according to claim 2, wherein the frequency of the energy is in a range of 750 kHz to 8 MHz or a range of 8 MHz to 20 MHz.

10. The non-invasive ultrasound treatment system according to claim 2, wherein the transducer is coupled to the variable depth element and is configured to focus the energy emitted by the surface of the transducer to any depth in more than one region of interest.

11. The non-invasive ultrasound treatment system according to claim 2, wherein the reflective surface comprises at least one mirror.

12. The non-invasive ultrasound treatment system according to claim 11, wherein the mirror is substantially flat in shape.

13. The non-invasive ultrasound treatment system according to claim 11, wherein the mirror is curved in shape.

14. The non-invasive ultrasound treatment system according to claim 2, wherein the transducer is configured with spatial control to change at least one of a distance from the transducer to the reflective surface, and an angle of the energy delivered into the region of interest.

15. The non-invasive ultrasound treatment system according to claim 2, wherein the transducer is configured in a curved manner.

16. The non-invasive ultrasound treatment system according to claim 2, wherein the at least one transduction element is a plurality of transduction elements configured to be activated by a plurality of frequencies separated by at least one phase delay.

17. The non-invasive ultrasound treatment system according to claim 2, wherein the controller further comprises a display unit for displaying at least one of imaging information, positional information and temperature information of a treatment region.

18. The non-invasive ultrasound treatment system according to claim 2, wherein the controller further comprises a robotic arm arrangement for controlling movement of the variable depth.

19. The non-invasive ultrasound treatment system according to claim 18, wherein the controller movement of the variable depth transducer system is configured to create a plurality of lesions at varying depths in the region of interest.

20. The non-invasive ultrasound treatment system according to claim 2, wherein the energy is focused to a first depth in the superficial region and the energy is focused to a second depth in the subcutaneous region, wherein the first depth and the second depth is in a range from 0 mm to 5 cm, and the first depth is less than the second depth.

* * * * *

UNITED STATES PATENT AND TRADEMARK OFFICE
CERTIFICATE OF CORRECTION

PATENT NO. : 10,039,938 B2
APPLICATION NO. : 14/264732
DATED : August 7, 2018
INVENTOR(S) : Peter G. Barthe et al.

Page 1 of 2

It is certified that error appears in the above-identified patent and that said Letters Patent is hereby corrected as shown below:

In the Specification

Column 1, Line 46, "surgeries ma also" should be --surgeries may also--.

Column 1, Line 56, "snot" should be --spot--.

Column 2, Line 8, "tinting" should be --timing--.

Column 4, Line 46, "303" should be --308--.

Column 4, Line 59, "device ma comprise" should be --device may comprise--.

Column 4, Line 63, "and/hr" should be --and/or--.

Column 4, Line 64, "and/of" should be --and/or--.

Column 5, Line 60, "of as transduction" should be --of a transduction--.

Column 5, Line 62, "can" should be --is--.

Column 6, Line 11, "to/front" should be --to/from--.

Column 7, Line 22, "far" should be --for--.

Column 7, Line 50, "far" should be --for--.

Column 8, Line 67, "an planar" should be --any planar--.

Column 9, Line 12, "exemplar" should be --exemplary--.

Signed and Sealed this
Twenty-third Day of July, 2019

Andrei Iancu
*Director of the United States Patent and Trademark Office*

CERTIFICATE OF CORRECTION (continued)
U.S. Pat. No. 10,039,938 B2

Column 9, Line 60, "period or the" should be --period of the--.

Column 12, Line 20-21, "through connector" should be --through a connector--.

Column 12, Line 21, "compose" should be --comprise--.

Column 12, Line 35, "this" should be --thus--.

Column 12, Line 41, "maximally" should be --manually--.

Column 12, Line 41, "100" should be --1010--.

Column 13, Line 4, "niche" should be --probe--.

Column 13, Line 7, "rosy allow fin" should be --may allow for--.

Column 13, Line 46, "anther" should be --and/or--.

Column 13, Line 59, "invention, exemplary" should be --invention, an exemplary--.

Column 14, Line 16, "of" should be --or--.

Column 14, Line 32, "hungers" should be --imagers--.